United States Patent [19]

Finnerty et al.

[11] Patent Number: 4,952,500

[45] Date of Patent: Aug. 28, 1990

[54] CLONING SYSTEMS FOR RHODOCOCCUS AND RELATED BACTERIA

[75] Inventors: William R. Finnerty, Athens; Mary E. Singer, Decatur, both of Ga.

[73] Assignee: University of Georgia Research Foundation, Inc., Athens, Ga.

[21] Appl. No.: 151,319

[22] Filed: Feb. 1, 1988

[51] Int. Cl.$^5$ .................. C12P 21/00; C12N 15/00; C12N 1/22; C12R 1/32; C12R 1/04; C12R 1/365; C12R 1/465; C07H 15/12

[52] U.S. Cl. .................. 435/69.1; 435/172.3; 435/252.3; 435/320; 435/863; 435/826; 435/872; 435/886; 435/91; 536/27; 935/6; 935/22; 935/60; 935/72

[58] Field of Search .................. 435/91, 172.3, 252.1, 435/320, 69.1, 826, 863, 872, 886; 935/6, 9, 29, 22, 56, 61, 72; 536/27

[56] References Cited

U.S. PATENT DOCUMENTS 4,343,906  8/1982  Reusser et al. .................. 435/253
4,649,119  3/1987  Sinskey et al. .................. 435/317

OTHER PUBLICATIONS

Singer, M. E., 1986, Abstracts of the Annual Meeting of the American Society for Microbiology, Mar. 23-28, 1986, Abstract No. H-88, "Plasmid Transformation in *Arthrobacter* sp H13A", p. 142, col. 1.

C. Sensfuss, et al., "No Correlation Exists Between Conjugative Transfer of Autotrophic Character and That of Plasmids in *Norcardia opaca* Strains," J. Gen. Microbiol. 132: 997–1007 (1986).

Brownell and Denniston, "Genetics of the Nocardioform Bacteria in The Biology of the Actinomycetes," M. Goodfellow, et al. eds. pp. 201–228 (Academic Press, NY 1984).

Browness, et al., "The Development of a Rhodococcus–Actinophage Gene Cloning System," *Dev. Indust. Microbiol.*, 23:287–298 (1982).

Brownell, et al. "An Analysis of the Genome of Actinophage φEC", *Gene* 12:311–314, (1980).

Hopwood, et al. *Genetic Manipulation of Streptomyces, a Laboratory Manual*, The John Innes Foundation 1985, pp. 103–121 (1985).

Miwa, et al., "Cryptic Plasmids in Glutamic Acid Producing Bacteria", *Agric. Biol. Chem.* 48:2901–2903 (1984).

Singer, et al., "Microbial Desulfurization and Biosurfactant Production Strain Improvement Through Genetic Approaches", *Fif. Intl. Symp. Gen. Indust. Microorg.*, M. Alacevice, et al., eds. (May 1987).

Finnerty and Singer, "A Microbial Biosurfactant Physiology, Biochemistry, and Applications", *Devel. Indust. Microbiol.*, vol. 25, pp. 31–40 (1984).

*Primary Examiner*—Thomas G. Wiseman
*Assistant Examiner*—Richard C. Peet
*Attorney, Agent, or Firm*—Kilpatrick & Cody

[57] ABSTRACT

A plasmid transformation system for Rhodococcus was developed using an *Escherichia coli*-Rhodococcus shuttle plasmid. Rhodococcus sp. H13-A contains three cryptic indigenous plasmids, designated pMVS100, pMVS200 and pMVS300, of 75, 19.5 and 13.4 kilobases (Kb), respectively. A 3.8 Kb restriction fragment of pMVS300 was cloned into pIJ30, a 6.3 Kb pBR322 derivative, containing the *E. coli* origin of replication (ori) and ampicillin resistance determinant (bla) as well as a Streptomyces gene for thiostrepton resistance, tsr. The resulting 10.1 Kb recombinant plasmid, designated pMVS301, was isolated from *E. coli* DH1 (pMVS301) and transformed into Rhodococcus sp. AS-50, a derivative of strain H13-A, by polyethylene glycol-assisted transformation of Rhodococcus protoplasts and selection for thiostrepton-resistant transformants. This strain was deposited with the ATCC on Feb. 1, 1988 and assigned ATCC 53719.

The plasmid contains the Rhodococcus origin of replication. The plasmid and derivatives thereof can therefore be used to introduce nucleic acid sequences to and from Rhodococcus for subsequent expression and translation into protein. The isolated origin of replication can also be used in the construction of new vectors.

17 Claims, 2 Drawing Sheets

CLONING SYSTEMS FOR RHODOCOCCUS AND RELATED BACTERIA

The United States government has rights in this invention by virtue of Department of Energy grants, #DE-AS09-80ER-10683 and #DE-FG09-86ER13588.

BACKGROUND OF THE INVENTION

The present invention relates to cloning vectors for use in Rhodococcus and related bacteria.

Members of the genus Rhodococcus are gram-positive, aerobic, non-sporulating, partially acid-fast Actinomycetes, which were formerly classified as Nocardia, Mycobacterium, Gordona, Jensenia, or in the "rhodochrous" complex. Nocardia, Corynebacteria and Mycobacterium are closely related to Rhodococcus, each exhibiting nocardioform morphology, having mycolic acids, meso-diaminopimelic acid, arabinose and galactose in their cell walls and having a high G+C content (>59 mol %) in their cellular DNA. Most members of the genus are saprophytic soil organisms, although several pathogenic species exist, including R. bronchialis, a human pathogen, R. equi, an animal pathogen and R. fascians, a plant pathogen.

Rhodococci exhibit a wide range of metabolic activities including antibiotic production, amino acid production, degradation of alkanes and aromatic hydrocarbons, biotransformation of steroids and a number of xenobiotic compounds, lignin degradation, chemolithoautotrophic growth in the presence of hydrogen and carbon dioxide and production of biosurfactants.

Genetic studies in Rhodococcus have focused on mapping the R. erythropolis chromosome, with approximately 65 chromosomal markers established, using a natural mating and recombination system, as reported by Brownell et al., The Biology of the Actinomycetes, M. Goodfellow, eds., pp. 201–228 (Academic Press, N.Y. 1984). A lysogenic actinophage, φEC, a 47 Kb double stranded DNA phage, has been physically mapped by restriction analysis for potential use as a cloning vector in Rhodococcus, as described by Brownell, et al., Gene 12, 311–314 (1980) and Dev. Ind. Microbiol. 23, 287–298 (1982). Phage φEC can be transferred between fertile Rhodococcus strains either as a plasmid or as a prophage and phage φEC DNA can be transfected into R. erythropolis protoplasts. Native plasmids have been described by Reh in Zbl. Bakt. Suppl. 11, 577–583 (1981) and by Sensfuss, et al., in J. Gen. Microbiol. 132, 997–1007 (1986) in the hydrogen-oxidizing autotrophic strain Rhodococcus sp. (Nocardia opaca 1b). The self-transmissible trait, Aut+, encoding genes for autotrophic growth in this strain, was previously thought to be plasmid-localized, but is now considered to be a chromosomal trait. Thallium resistance is associated with large plasmids, (110–140 Kb) in two Aut+ strains described by Sensfuss, et al.

Although cloning vectors have been reported for a variety of Gram negative organisms, especially E. coli, and a few Gram positive organisms such as Corynebacterium and Bacillus, to date, no one has provided a vector which can be used to transfer foreign DNA into Rhodococcus for transcription and translation into protein.

It is therefore an object of the present invention to provide a cloning vector for transforming DNA into Rhodococcus.

It is another object of the present invention to provide a cloning vector which can be used as a shuttle vector between Rhodococcus and E. coli and other bacteria.

It is a further object of the present invention to provide a method and means for constructing additional cloning vectors for use in Rhodococcus and related bacteria.

SUMMARY OF THE INVENTION

A plasmid transformation system has been developed utilizing an Escherichia coli-Rhodococcus shuttle vector. The utility of the system is demonstrated using a wild-type soil isolate designated Rhodococcus sp. H13-A. This organism produces an extracellular glycolipid with surface-active properties and contains three cryptic indigenous plasmids, designated pMVS100, pMVS200 and pMVS300, of 75, 19.5 and 13.4 kilobases (Kb), respectively.

A 3.8 Kb restriction fragment of pMVS300 was cloned into pIJ30, a 6.3 Kb pBR322 derivative, containing the E. coli origin of replication (ori) and ampicillin resistance determinant (bla) as well as a Streptomyces gene for thiostrepton resistance, tsr. The resulting 10.1 Kb recombinant plasmid, designated pMVS301, was isolated from E. coli DH1 (pMVS301) and transformed into Rhodococcus sp. AS-50, a derivative of strain H13-A, by polyethylene glycol-assisted transformation of Rhodococcus protoplasts and selection for thiostrepton-resistant transformants. Rhodococcus sp. AS-50-1 (pMVS301) was deposited with the ATCC 53719 on Feb. 1, 1988 and assigned ATCC 53719. Thiostrepton-resistant transformants were also ampicillin resistant and contain pMVS301, which can be isolated and transformed back into E. coli.

The cloned 3.8 Kb fragment of Rhodococcus DNA in pMVS301 contains a Rhodococcus origin of replication, since the hybrid plasmid is capable of replication in both genera. The plasmid is identical in E. coli and Rhodococcus as determined by restriction analysis and is maintained as a stable, independent replicon in both organisms. Optimization of the transformation procedure resulted in transformation frequencies in the range of $10^5$ transformants per μg of pMVS301 DNA in Rhodococcus sp. H13-A and derivative strains.

The plasmid host range extends to strains of R. erythropolis, R. globulerus and R. equi. The plasmid pMVS301 has 14 unique restriction sites, some of which are useful for molecular cloning in Rhodococcus and other Actinomycetes. The plasmid can also be used in the construction of additional cloning vectors for use in Rhodococcus and other Actinomycetes.

DETAILED DESCRIPTION OF THE INVENTION

Figure 1:
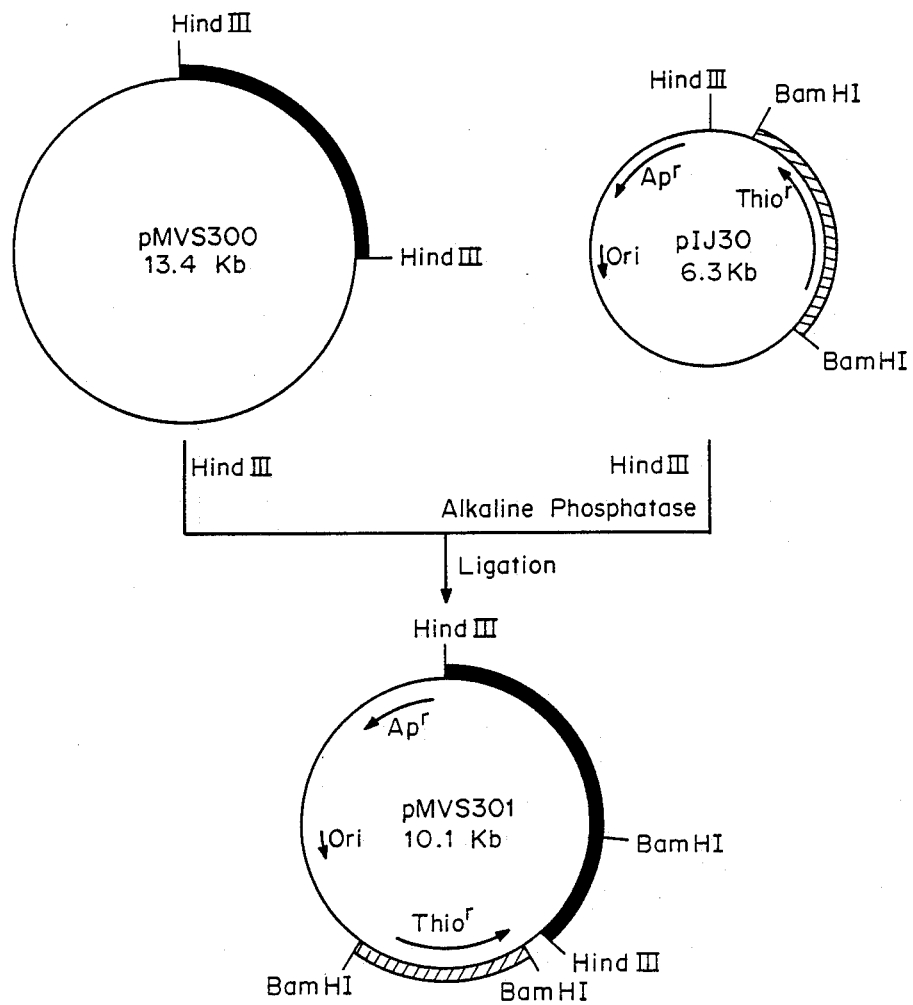
FIG. 1 diagrams the construction of the E. coli-Rhodococcus shuttle plasmid, pMVS301. The 3.8 Kb HindIII fragment (dark bar) of pMVS300 was cloned into pIJ30, which is a pBR322 derivative containing the E. coli origin of replication (ori) and bla gene (ampicillin resistance) and Streptomyces azureus DNA (cross-hatched area) with the tsr gene (thiostrepton resistance). Arrows indicate direction of transcription.

Rhodococcus sp. H13-A was isolated from soil by screening bacterial isolates for reduction of the tensiometric properties of spent culture broths following growth on hexadecane or crude oil, as described by Finnerty and Singer, *Dev. Ind. Microbiol.* 25, 31–40 (1984). The organism is unusual in its production of a cellular and extracellular glycolipid surfactant which is produced only during growth on n-alkanes, C10 to C20. As described by Singer et al in *Proc. Fifth Intern. Symp. Gen. Indust. Microorg.*, M. Alacevi et al, ed. (May 1987), the bacteria, originally designated Arthrobacter H13-A contains three cryptic plasmids, pMVS100, pMVS200, and pMVS300, originally described as having molecular sizes of 45, 18.3, and 14.7 Kb, respectively. Plasmid encoded antibiotic resistance markers are not detected in H13-A, the organism demonstrating sensitivity to a number of antibiotics including ampicillin and thiostrepton. Plasmid-curing by growing in the presence of 50 μg acridine orange/ml for 18 h and screening for survivors yields strains lacking pMVS300.

A plasmid transformation system in Rhodococcus which involves uptake of plasmid DNA by protoplasts in the presence of polyethylene glycol was developed using one plasmid from this unique soil isolate, pMVS300. The transformation system is highly efficient, yielding greater than $10^5$ transformants per μg of Rhodococcus-derived plasmid DNA. Transformation is less efficient with *E. coli*-derived plasmid DNA, indicating the presence of a restriction/modification system in Rhodococcus. This transformation system was adapted from methods designed for the protoplast transformation of Streptomyces, using the same protoplasting and regeneration media. Differences in the present system include growth of cells in the presence of ampicillin rather than glycine, longer treatment times with lysozyme at a higher concentration and transformation in the presence of PEG 8000 rather than PEG 1000.

*E. coli*-Rhodococcus shuttle plasmids, pMVS301, pMVS302, pMVS301KC and pMVS301KA were constructed as a prerequisite to the development of a plasmid transformation system in Rhodococcus. These bifunctional plasmids fulfil the requirements for stable, independent replication in both Rhodococcus and *E. coli* and have two selectable antibiotic resistance markers, encoding ampicillin resistance and thiostrepton resistance. The construction of these shuttle plasmids allow cloning and molecular characterization of hybrid plasmids in *E. coli* and further genetic manipulation and molecular analyses in *E. coli* or in Rhodococcus. These plasmids could not have been constructed in the absence of the Rhodococcus origin of replication derived from pMVS301.

Both antibiotic resistance markers, the Streptomyces thiostrepton resistance gene, tsr, and the *E. coli* ampicillin resistance gene, bla, were expressed in Rhodococcus transformants. However, thiostrepton resistance is not a selectable marker in *E. coli* due to outer membrane exclusion of thiostrepton by gram-negative bacteria. The level of bla gene expression differed in *E. coli* and Rhodococcus transformants, with lower β-lactamase activity detected in Rhodococcus transformants. This could be attributed to lower copy number of the plasmids, lower levels of bla gene transcription or translation, or to increased rates of RNA or protein degradation in Rhodococcus. In Rhodococcus, β-lactamase activity is located exclusively in the extracellular medium, indicating that the organism can process and secrete heterologous proteins.

Rhodococcus transformants containing pMVS302 exhibit higher levels of ampicillin resistance and β-lactamase activity than those containing pMVS301. The two plasmids differ only in the orientation of the cloned fragment of Rhodococcus DNA located upstream of the bla gene. Expression of the bla gene in *E. coli* transformants is independent of the orientation of the cloned Rhodococcus DNA, with similar levels of ampicillin resistance and β-lactamase activity in transformants containing either plasmid. The orientation-dependent expression of the *E. coli* bla gene in Rhodococcus indicates that bla gene transcription occurs from a Rhodococcus promoter in the cloned fragment rather than from its own promoter. Alternatively, pMVS302 may have a higher copy number than pMVS301 in Rhodococcus. This is unlikely since both plasmids contain the same origin of replication. In addition, estimates of plasmid copy number gels of total DNA preparations indicate that pMVS301 and pMVS302 have similar copy numbers in Rhodococcus.

Several Rhodococcus species were transformed with the shuttle plasmid at high efficiencies, yielding stable plasmid transformants. The plasmid host range includes strains of *R. erythropolis*, *R. globerulus* and *R. equi*. The coryneform bacteria tested were not stably transformed with the plasmid, although protoplasts were readily formed and regenerated.

Plasmid pMVS301 has several potentially useful cloning sites. There are a number of unique restriction enzyme sites which can be used, other than around the XhoI site where the Rhodococcus origin of replication is located. Cloning at the BglII site has been demonstrated. The unique PstI site in the bla gene may be useful for self-cloning in Rhodococcus by insertional activation of the ampicillin resistance determinant. Several other unique sites on the vector, such as the SphI site, may be useful for non-selectional cloning in either Rhodococcus or *E. coli*.

This is the first plasmid transformation system and demonstration of heterologous gene expression in Rhodococcus. The Rhodococcus shuttle vectors constructed are useful for molecular cloning in this genus as well as for cloning Actinomycete genes of interest, including genes from the medically important pathogens, Nocardia and Mycobacterium.

Even though Mycobacterium DNA has been cloned in both *E. coli* and Streptomyces, the present invention has advantages. In general, mycobaterial genes are weakly expressed from their own promoters in *E. coli*. Cloned *M. bovis* BCG DNA is expressed from its own transcriptional and translational signals more efficiently in *S. lividans* than in *E. coli*. Streptomyces, a spore-forming, mycelial Actinomycete with a G+C content of 69–73 mol %, readily recognizes heterologous promoters and substantial progress has been made in the development of molecular cloning and genetic transfer systems in this organism. However, many Streptomyces genes are not transcribed efficiently in *E. coli* due to the absence of promoter recognition and differences in promoter structure. The Rhodococcus host/vector system described may provide an alternative for molecular cloning in the Actinomycetes.

Rhodococcus sp. H13-A is a nonpathogenic, nonmycelial and nonsporulating strain with a G+C content of 66 mol % (59-69 mol % G+C for the genus, Rhodococcus), which falls within the range reported for the closely related Mycobacterium (62-70 mol % G+C) and Nocardia (60-69 mol % G+C). The expression of genes in Rhodococcus both from *E. coli* and Streptomyces has been demonstrated, indicating that Rhodococcus may be a useful host for the expression of Actinomycete DNA from its own regulatory signals.

The following is a detailed description of the construction and characterization of the Rhodococcus strains containing genetically engineered plasmids which can be used in the cloning and expression of homologous and heterologous genes into Rhodococcus and related bacteria such as Nocardia, Streptomyces, Mycobacteria, and other Actinomycetes.

The general strategy employed for construction of a shuttle vector is shown in FIG. 1. The cloning vector, pIJ30, is an *E. coli* replicon derived from pBR322, containing an *E. coli* origin of replication (ori), *E. coli* gene for ampicillin resistance (bla) and a gene for thiostreption resistance (tsr), derived from *Streptomyces azureus*, described by Thompson et al., Gene 20, 51–62 (1982). The native Rhodococcus plasmid, pMVS300, was digested with HindIII, yielding restriction fragments of 3.8 and 9.6 Kb. The entire restriction digest was then ligated to the HindIII-digested, alkaline phosphatase-treated vector, pIJ30, which has a single HindIII restriction site. The ligation mixture was used to transform *E. coli* DH1, selecting for ampicillin resistance. Ampicillin-resistant transformants were analyzed by colony hybridization with $^{32}$P-labeled pMVS300 DNA to detect recombinant plasmids. Plasmid content of presumptive transformants was verified by small-scale plasmid preparation, followed by digestion with the appropriate restriction enzyme.

Two 10.1 Kb recombinant plasmids were detected which contained the pMVS300-derived 3.8 Kb HindIII restriction fragment cloned in two different orientations relative to the internal BamHI cleavage site. These two plasmids were designated pMVS301 (FIG. 1) and pMVS302. Recombinant plasmids containing the 9.6 Kb HindIII restriction fragment of pMVS300 were not detected among the transformants tested. Southern hybridization experiments confirmed that the 3.8 Kb HindIII fragment cloned in pMVS301 and pMVS302 was derived from pMVS300.

Plasmid Transformation in Rhodococcus

Transformation of Rhodococcus sp. AS-50 with pMVS301 initially yielded thiostrepton-resistant transformants at low transformation frequencies (<100 transformants per µg DNA), with significantly higher frequencies resulting from optimization of the transformation procedure. Thiostrepton-resistant transformants were not detected using pIJ30 as donor DNA. Likewise, spontaneous thiostrepton-resistant transformants of strain AS-50 were not detected when plasmid DNA was deleted in control transformation experiments.

Thiostrepton-resistant transformants of strain AS-50 were characterized to verify plasmid content and to examine the phenotypic expression of the plasmid antibiotic resistance markers. The transformants were resistant to thiostrepton (>500 µg/ml) and to ampicillin (30 µg/ml). The host strain, AS-50, was sensitive to 0.05 µg/ml thiostrepton and 5 µg/ml ampicillin. Each of the transformants contained the 10.1 Kb plasmid, pMVS301. Strain AS-50-1 (pMVS301), a representative transformant, contained pMVS301 as well as the native plasmids, pMVS100 and pMVS200, which were present in the host strain, AS-50, as shown by agarose gel electrophoresis of plasmid DNA isolated from Rhodococcus sp. H13-A; strain AS-7; strain AS-50; strain AS-50-1 (pMVS301); *E. coli* DH1 (pMVS301) and *E. coli* 1830 (pIJ30). This strain AS-50-1 (pMVS301) was deposited with the American Type Culture Collection, Rockville, Md. on Feb. 1, 1988 and assigned ATCC 53719.

*E. coli* DH1 was transformed with plasmid DNA prepared from Rhodococcus sp. AS-50-1 (pMVS301) selecting for ampicillin-resistant transformants. The resulting transformants also contained pMVS301, as demonstrated by agarose gel electrophoresis. The plasmid was again isolated from *E. coli* and transformed into Rhodococcus sp. AS-50, with isolation of thiostrepton-resistant transformants harboring pMVS301.

Restriction analysis shows that pMVS301 does not undergo rearrangement or deletion in either *E. coli* or Rhodococcus. An additional ClaI restriction site, located in the 3.8 Kb Rhodococcus DNA fragment, was identified in the plasmid only when isolated from Rhodococcus transformants. Since ClaI restriction sites are subject to methylation in dam+ *E. coli* strains, this site was presumably methylated in *E. coli* DH1 and not in Rhodococcus. With this exception, plasmid restriction patterns were identical regardless of plasmid source, using several different restriction enzymes.

Transformation of Rhodococcus sp. AS-50 with pMVS302 DNA also yielded thiostrepton-resistant transformants. pMVS302 differs from pMVS301 only in the orientation of the cloned 3.8 Kb HindIII fragment of pMVS300. These transformants contained pMVS301 and were resistant to >500 µg/ml thiostrepton and >750 µg/ml ampicillin. Plasmid DNA isolated from Rhodococcus sp. AS-50-2-(pMVS302), a thiostrepton-resistant transformant containing pMVS301, was used to transform *E. coli* DH1. The resulting ampicillin-resistant transformants contained pMVS302. Restriction analyses demonstrated that neither deletion nor rearrangement of pMVS302 occurred in *E. coli* or Rhodococcus.

Two derivatives of pMVS301 containing a kanomycin-resistance determinant, pMVS301KA and pMVS301KC, were constructed by cloning the 1.5 Kb kanomycin-resistance fragment from the plasmid pUC4K into the BglII site in pMVS301. The kanomycin-resistance fragment was isolated from pUC4K by digestion with BamH1 and purification of the 1.5 Kb BamH1 fragment by agarose gel electrophoresis and electroelution. This fragment was ligated to pMVS301 which had been linearized by BglII digestion. The ligation mixture was then transformed into *E. coli* DH1 selecting for ampicillin and kanomycin resistant transformants.

Plasmids pMVS301KA and pMVS301KC are the 11.6 Kb recombinant plasmids containing the kanomycin-resistant fragment derived from pUC4K cloned in two different orientations. These two plasmids were transformed into Rhodococcus sp. E1A1 (pMVS100). Rhodococcus E1A1-1 (pMVSA301KA) in Rhodococcus E1A1-2 (pMVS301KC) are thiostrepton, ampicillin, and kanomycin resistant transformants which contain the shuttle plasmids derivatives pMVS301KA and pMVS301KC, respectively. These plasmid derivatives are transferrable between *E. coli* and Rhodococcus and can be used for cloning in either *E. coli* or Rhodococcus.

Optimization of Conditions for Plasmid Transformation in Rhodococcus.

Rhodococcus transformants were not detected when PEG was omitted from the transformation mixture or when intact cells rather than protoplasts were used in the transformation procedure. PEG concentrations above 25% (wt/vol.) were inhibitory and higher transformation frequencies were obtained using PEG 8000 rather than PEG 3350 or PEG 1000. Treatment of cells with ampicillin (200 µg/ml) prior to lysozyme digestion of the cell wall was required for efficient protoplast formation. Protoplast regeneration efficiency was 75% for Rhodococcus sp. H13-A strains. The maximum transformation frequency obtained was $2 \times 10^5$ to $3 \times 10^5$ transformants/µg DNA, using Rhodococcus-derived pMVS301 or pMVS302 DNA to transform Rhodococcus sp. As-50 (Table 1). Transformation frequencies were approximately 500-fold lower using *E. coli*-derived pMVS301 or pMVS302 DNA to transform Rhodococcus sp. AS-50 (Table 1). These results indicate the presence of restriction/modification system in the Rhodococcus recipient, which can be overcome by using plasmid DNA isolated from Rhodococcus for transformation.

Similar transformation frequencies were obtained using the wild-type strain, Rhodococcus sp. H13-A or strains AS-50 and AS-7 as recipients (Table 1). Transformation of Rhodococcus sp. H13-A or strain AS-7 with pMVS301 resulted in the loss of pMVS300, indicating incompatibility between pMVS300 and pMVS301. Homologous recombination of pMVS300 with pMVS301, which would result in the generation of a larger plasmid, was not detected in strain H13-A or AS-7 transformants. No homology was detected between the 3.8 Kb HindIII fragment of pMVS301 and pMVS100 or pMVS200 by Southern hybridization experiments.

TABLE 1

Bacterial Strains and Plasmids

| Strain | Plasmid Markers |
|---|---|
| Rhodococcus sp. H13-A(pMVS100, pMVS200,pMVS300) | Cryptic |
| Rhodococcus sp. AS-7(pMVS100, pMVS300) | Cryptic |
| Rhodococcus sp. AS-50(pMVS100, MVS200) | Cryptic |
| Rhodococcus sp. E1A1(pMVS100) | Cryptic |
| Rhodococcus sp. AS-50-1(pMVS100, pMVS200,pMVS301) | Ap ®,Thio ®(pMVS301) |
| Rhodococcus sp. AS-50-2(pMVS100, pMVS200,pMVS302) | Ap ®,Thio ®(pMVS302) |
| Rhodococcus sp. E1A1-1(MVS100, pMVS301KA) | Ap ®,Thio ®,Km ® |
| Rhodococcus sp. E1A1-2(pMVS100, pMVS301KC) | Ap ®,Thio ®,Km ® |
| *E. coli* DH1 | — |
| *E. coli* 1830(pIJ30) | Ap ®,Thio ® |
| *E. coli* DH1(pMVS301) | Ap ®,Thio ® |
| *E. coli* DH1(pMVS302) | Ap ®,Thio ® |
| *E. coli* DH1(pMVS301KA) | Ap ®,Thio ®,Km ® |
| *E. coli* DH1(pMVS301KC) | Ap ®,Thio ®,Km ® |

Host Range of Shuttle Vector

Representatives of the genus Rhodococcus and several members of the coryneform group of bacteria were transformed with the shuttle plasmid, pMVS301, using the protoplast transformation method developed for Rhodococcus sp. H13-A. The results are shown in Table 2. Thiostrepton-resistant transformants were obtained with Rhodococcus erythropolis ATCC 4277, *R. globerulus (N. globerula)* ATCC 15903 and *R. equi (N. restrictus)* ATCC 14887-1 at frequencies similar to those obtained with strain H13-A and derivatives (Table 3). Transformants were obtained at a 33-fold lower frequency in *R. erythropolis (Nocardia calcarea)* ATCC 19369. Thiostrepton-resistant transformants of these strains were stable upon repeated transfer to thiostrepton-containing medium. In addition, all exhibited ampicillin resistance at levels ranging from 25–100 µg/ml, depending on the strain.

TABLE 2

Plasmid Transformation of Rhodococcus Protoplasts

| Recipient Strain | Donor DNA | Source of Donor DNA | Transformation Frequency (Transformants /µg DNA) |
|---|---|---|---|
| R. sp. AS-50 | pMVS301 | R. sp. AS-50-1 (pMVS301) | $1.9 \times 10^5$ |
| R. sp. AS-50 | pMVS302 | R. sp. AS-50-2 (pMVS302) | $3.3 \times 10^5$ |
| R. sp. H13-A | pMVS301 | R. sp. AS-50-1 (pMVS301) | $1.0 \times 10^5$ |
| R. sp. AS-7 | pMVS301 | R. sp. AS-50-2 (MVS302) | $8.3 \times 10^4$ |
| R. sp. AS-50 | pMVS301 | *E. coli* DH1 (pMVS301) | $3.6 \times 10^2$ |
| R. sp. AS-50 | pMVS302 | *E. coli* DH1 (MVS302) | $3.8 \times 10^2$ |

Thiostrepton-resistant transformants were not detected in *R. rhodochrous* ATCC 13808, or in the coryneform bacteria, *Arthrobacter globiformis, Corynebacterium glutamicum*, or *Brevibacterium linens* (Table 3). Unstable transformants were obtained with *R. globerulus (Nocardia globulera)* ATCC 19370 and *Arthrobacter simplex* BRRL 35581, with loss of thiostrepton resistance following one or more transfers to thiostrepton-containing medium.

TABLE 3

Transformation of Nocardioform and Cornyeform Bacteria with the *E. coli*-Rhodococcus Shuttle Plasmid, pMVS301

| Bacterial Strain | Transformation Frequency (Transformants /µg DNA) |
|---|---|
| Rhodococcus strains: | |
| R. erythropolis ATCC 4277 | $6.4 \times 10^5$ |
| R. erythropolis (Nocardia clacarea) ATCC 19369 | $7.8 \times 10^3$ |
| R. globerulus (N. globerula) ATCC 15903 | $2.4 \times 10^5$ |
| R. globerulus (N. globerula) ATCC 19370 | $<1.0$ |
| R. equi (N. restrictus) ATCC 14887-1 | $3.4 \times 10^6$ |
| R. rhodochrous ATCC 13808 | 0 |
| Coryneform Bacteria: | |
| Arthrobacter simplex BRRL 35581 | $1 \times 10^2$ |
| Arthrobacter globiformis ATCC E8010 | 0 |
| Cornebacterium glutamicum ATCC 13059 | 0 |
| Brevibacterium linens ATCC 9172 | 0 |

The conditions for the formation of protoplasts and the transformation of plasmid DNA were not optimized for these strains and transformation frequencies may reflect non-optimal conditions for any of several steps in the procedure. However, all strains tested formed viable protoplasts which regenerated on R2YE medium using the conditions established for Rhodococcus sp. H13-A.

Shuttle Vector Stability

The shuttle plasmids, pMVS301 and pMVS302, exhibited less than a 0.1% loss per generation in *E. coli* during growth under non-selective conditions. In Rhodococcus sp. AS-50-1 (pMVS301), the plasmid exhibited a 1.0% loss per generation, while in Rhodococcus sp. AS-50-2 (pMVS302), the plasmid was lost at a frequency of 7.3% per generation during growth under non-selective conditions. Rhodococcus transformants were routinely grown in medium containing 50 µg/ml thiostrepton. Under these selective conditions, thiostrepton resistance was maintained as a stable, plasmid-borne trait.

β-lactamase Activity in Transformants

Rhodococcus transformants containing pMVS301 or pMVS302 exhibited ampicillin resistance at levels 6-fold and 150-fold higher, respectively, than that of the parent strain, AS-50, as shown in Table 4. The minimal inhibitory concentration (MIC) of ampicillin for Rhodococcus strain AS-50-2 (pMVS302) was 30-fold greater than that for strain AS-50-1 (pMVS301). The level of thiostrepton resistance, however, was similar in both strains (Table 4). The MIC of ampicillin was >1000 µg/ml for the *E. coli* strains DH1 (pMVS301) and DH1 (pMVS302). This MIC was 20 to 30-fold higher than that for Rhodococcus sp. AS-50-1 (pMVS301); while Rhodococcus sp. AS-50-2 (pMVS302) exhibited elevated levels of ampicillin resistance similar to those observed in the *E. coli* transformants.

TABLE 4

Minimal Inhibitory Concentrations (MIC) of Antibiotics for *E. coli* and Rhodococcus Strains

| Strain | Ampicillin (MIC) (µg/ml) | Thiostrepton MIC (µg/ml) |
|---|---|---|
| R. sp. H13-A | <5 | 0.05 |
| R. sp. AS-50 | <5 | 0.05 |
| R. sp. AS-50-1 (pMVS301) | 30–50 | >500 |
| R. sp. AS-50-2 (pMVS302) | 750–1000 | >500 |
| *E. coli* DH1 | <5 | NS |
| *E. coli* DH1 (pMVS301) | >1000 | NS |
| *E. coli* DH1 (pMVS302) | >1000 | NS |

NS = not sensitive

β-lactamase activity was measured in the cells and extracellular growth medium of *E. coli* and Rhodococcus transformants to correlate levels of ampicillin resistance with β-lactamase activity. β-lactamase activity was exclusively extracellular in Rhodococcus transformants, with no detectable cell-associated activity, demonstrated in Table 5. Cell-free extracts prepared by sonication of Rhodococcus cells showed no detectable β-lactamase activity. In *E. coli* transformants, 70% of the β-lactamase activity was cell-associated and 30% was present in the growth medium. The specific activity of β-lactamase in pMVS301-and pMVS302-containing transformants was 3-fold higher than that of the host strain, *E. coli* DH1. Total β-lactamase activity was 7- and 47-fold higher in *E. coli* transformants containing pMVS301 and pMVS302, respectively, than in the corresponding Rhodococcus transformants, indicating lower levels of bla gene expression in Rhodococcus than in *E. coli*. The relative β-lactamase activity in Rhodococcus strains correlated directly with the level of ampicillin resistance in the respective transformants. The expression of the *E. coli* bla gene in Rhodococcus appears dependent on the orientation of the 3.8 Kb HindIII Rhodococcus DNA fragment in the shuttle plasmid, suggesting that the bla gene is transcribed from a promoter in that segment of DNA.

TABLE 5

β-lactamase Activity in *E. coli* and Rhodococcus Strains

| | β-lactamase Activity Units[a]/mg Cell Protein | | |
|---|---|---|---|
| Strain | Cellular | Extracellular | Total |
| R. sp. AS-50 | ND | 0.03 | 0.03 |
| R. sp. AS-50-1 (pMVS301) | ND | 0.33 | 0.33 |
| R. sp. AS-50-2 (pMVS302) | ND | 2.73 | 2.73 |
| *E. coli* DH1 | .30 | 0.04 | 5.34 |
| *E. coli* DH1 (pMVS301) | 10.70 | 5.06 | 5.76 |
| *E. coli* DH1 (pMVS302) | 12.50 | 6.42 | 18.92 |

ND = not detected
[a]1 unit of β-lactamase activity equals 1 µmole PADAC hydrolyzed per min at 30° C.

Restriction Analysis of pMVS301

Figure 2:
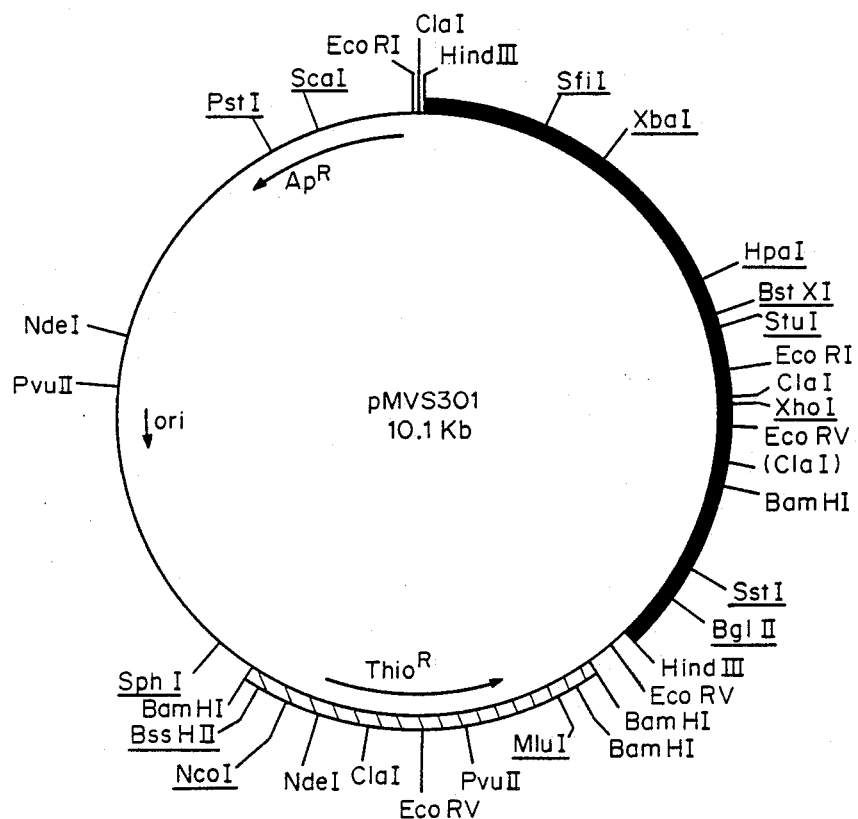
FIG. 2 is a partial restriction map of pMVS301. Unique restriction endonuclease cleavage sites are underlined. Dark bar represents Rhodococcus DNA with Rhdococcus origin of replication. Cross-hatched area represents Streptomyces DNA carrying the tsr gene (thiostrepton-resistance). Fine, solid line represents DNA from pBR322 with the *E. coli* origin of replication (ori) and bla gene (ampicillin resistance). Arrows denote direction of transcriptions. The ClaI restriction site in the Rhodococcus DNA, designated (ClaI), is not cleaved in DNA isolated from *E. coli* DH1 (pMVS301).

A partial restriction endonuclease cleavage map of pMVS301 is shown in FIG. 2. The plasmid has 14 unique restriction sites, 8 of which are found in the cloned DNA fragment containing the Rhodococcus origin of replication. The pBR322 portion of the plasmid has 3 unique restriction sites, PstI, ScaI and SphI. The 1.8 Kb BamHI fragment which contains the thiostrepton resistance determinant has 3 unique restriction sites: MluI, determined from tsr sequence data, BssHII and NcoI, determined by restriction mapping to lie upstream of the known tsr coding sequence. The known restriction endonuclease cleavage sites of pMVS301 are listed in Table 6.

TABLE 6

Restriction Endonuclease Cleavage Sites in pMVS301

| Unique Restriction Sites: | PstI, ScaI, SphI, MluI, BssHII, BglII, HpaI, StuI, XhoI, SfiI, NcoI, BstXI, SstI, XbaI |
|---|---|
| Two Restriction Sites: | HindIII, EcoRI, NheI, NdeI, ApaI, PvuII, BsmI, BstEII |
| Three Restriction Sites: | SspI, StyI, EcoRV, NruI, SmaI |
| Multiple Restriction Sites: | BamHI, ClaI, XmaIII, PvuI, AvaI, SalI, SstII, XmaI |
| No Restriction Sites: | SnaBI, SpeI, KpnI, NotI, NsiI, AatI, AsuII, CvnI |

Materials and Methods used in the above-described construction and characterization of the Rhodococcus strains and plasmids.

Bacterial Strains and Plasmids

The bacterial strains and plasmids used are shown in Table 1. Rhodococcus sp. H13-A, a wild-type soil isolate, is identified as a Rhodococcus sp. based on cell wall chemotype, cellular lipid analyses and biochemical tests according to Bergey's Manual. Rhodococcus sp. AS-7 is a pMVS200-cured derivative of Rhodococcus sp. H13-A and was used as the source of pMVS300 DNA, as depicted in FIG. 1. Rhodococcus sp. AS-50 is a pMVS300-cured derivative of strain H13-A and was used as the source of pMVS200 DNA.

*E. coli* DH1, which was used as the host for plasmid transformation, and *E. coli* 1830 (pIJ30), which was used as a source of pIJ30 DNA, were obtained from Apcel Ltd., Slough, U.K.

The coryneform bacteria, *Arthrobacter globiformis* ATCC E8010, *Corynebacterium glutamicum* ATCC 13059 and *Brevibacterium linens* ATCC 9172 were obtained from the American Type Culture Collection (ATCC). *Arthrobacter simplex*, BRRL 35581 was obtained from Apcel, Ltd., Slough, U.K.

Rhodococcus strains, *R. equi* (*Nocardia restrictus*) ATCC 14887-1, *R. globerulus* (*N. globerula*) ATCC 15903, *R. globerulus* (*N. globeruls*) ATCC 19370, and *R. erythropolis* (*N. calcarea*) ATCC 19369 were obtained from George Brownell, Medical College of Georgia, Augusta, Ga. *R. erythropolis* ATCC 4277 and *R. rhodochrous* ATCC 13808 were type strains obtained from ATCC.

Growth Conditions and Culture Media

Rhodococcus strains were grown at 30° C. on NBYE medium, containing 0.8% (wt/vol) nutrient broth (Difco) and 0.5% (wt/vol) yeast extract (Difco). NBYE was supplemented with 1.5% (wt/vol) Bacto-agar (Difco) for growth on solid medium. The hypertonic protoplast regeneration medium, R2YE, is described by Hopwood, et al., in *Genetic manipulation of Streptomyces*. A laboratory manual. The John Innes Foundation, Norwich, U.K. (1985). R2YE soft-agar overlays contain R2YE medium plus 0.6% Bacto-agar. Protoplast buffer (P-buffer) is a hypertonic medium used for protoplast preparation and transformation.

*E. coli* strains were grown at 37° C. on Luria-Bertani (LB) medium or LB medium supplemented with 1.5% Bacto-agar for growth on solid medium. Liquid cultures were agitated at 250 RPM for *E. coli* strains, or 300 RPM for Rhodococcus strains, on a rotary shaker-incubator.

Thiostrepton, obtained from Mr. Salvadore Lucania, Squibb Institute of Medical Research, Princeton, N.J., was prepared in dimethylsulfoxide.

Plasmid-curing Methods

Rhodococcus sp. H13-A was grown in the presence of 50 $\mu$g/ml acridine orange or 500 $\mu$g/ml sodium dodecyl sulfate (SDS) for 18 h. Surviving cells were plated onto NBYE-agar and were screened for plasmid loss.

Isolation of Plasmid DNA

Plasmid DNA was isolated from *E. coli* by the alkaline lysis method of Birnboim and Doly, Nucl. Acids Res. 7,1513-1523 (1979) and was purified by centrifugation in cesium chloride-ethidium bromide density gradients (ew). The boiling method of Holmes and Quigley, *Anal. Biochem.* 114,193-197 (1981) was used for rapid, small-scale isolation of *E. coli* plasmid DNA.

The following procedure was devised for large-scale isolation of plasmid DNA from Rhodococcus. Exponential-phase cells were harvested by centrifugation for 10 min at 6500$\times$g and were washed once in 10 mM Tris, 1 mM EDTA buffer, pH 8.0 (TE buffer). The cells were incubated at 37° C. for 2 h in a buffer containing 0.05M Tris, 0.01M EDTA, 0.05M NaCl and 20% (wt/vol) sucrose, pH 8.0, plus 5 mg/ml lysozyme. Cells were then lysed in 3.0% (wt/vol.) SDS in 0.05M Tris-chloride buffer, pH 12.6, at 55° C. for 2 h. Chromosomal DNA was precipitated with 5M potassium acetate-acetate buffer, pH 4.8, followed by centrifugation at 10,000$\times$g for 30 min. Plasmid DNA was precipitated from the resulting supernatant solution with isopropanol and purified by centrifugation in cesium chloride-ethidium bromide density gradients according to the method of Maniatis, et al., *Molecular cloning. A laboratory manual.* (Cold Spring Harbor Laboratory, N.Y. (1982).

The same procedure was scaled down for use with 1.5 ml of exponential phase NBYE-grown cells for small-scale preparation of plasmid DNA from Rhodococcus, eliminating the final cesium chloride-ethidium bromide density gradient centrifugation.

Plasmid Transformation

*E. coli* DH1 was transformed by the method of Hanahan, *J. Mol.Biol.* 166, 557-580 (1983). Transformants were selected on LB-agar plates containing 100 $\mu$g/ml ampicillin.

Rhodococcus Protoplast Preparation

Mid-exponential phase NBYE-grown cells were grown for 2 h in the presence of ampicillin (200 $\mu$g/ml). Cells were harvested in 5.0 ml portions by centrifugation at 1600$\times$g for 5 min at 25° C., washed once with P-buffer, centrifuged, and suspended in 1.0 ml P-buffer containing 10 mg/ml lysozyme and incubated 2 h at 35° C. with intermittent agitation. This cell suspension was diluted with P-buffer, centrifuged, washed once in P-buffer and centrifuged again. The resulting pellet containing protoplasts and intact cells was suspended in 150 $\mu$l P-buffer, and was used immediately for transformation. The percentage of protoplasts in the preparation was determined by differential plate counts on R2YE regeneration medium and on NBYE medium, or by microscopic counts.

Transformation of Rhodococcus Protoplasts

Freshly-prepared protoplasts were diluted in P-buffer to a density of $2.0\times10^7$ per ml. The protoplast suspension (100 $\mu$l) was mixed with 0.075-0.375 $\mu$g plasmid DNA in 1 to 5 $\mu$l of TE buffer. 25% (wt/vol.) PEG 8000 (Sigma Chemical Co., St. Louis, Mo.) in P-buffer (200 $\mu$l) was added and gently mixed. After 10 min at 25° C., the protoplast suspension was diluted with P-buffer and plated immediately onto freshly-prepared and dehydrated R2YE-agar plates. The plates were overlaid with R2YE soft-agar containing 50 $\mu$g/ml thiostrepton, after a 24 h regeneration period at 30° C., to select for thiostrepton-resistant transformants. Transformants were screened for ampicillin resistance by replica-plating to NBYE medium containing ampicillin (30 $\mu$g/ml).

Determination of Plasmid Stability

Rhodococcus and *E. coli* plasmid-containing strains were grown under non-selective conditions on NBYE- or LB-medium, respectively, for 24-30 generations and were then plated onto the same medium. 500 colonies were scored by replica-plating for resistance to ampicillin (100 $\mu$g/ml for *E. coli*, 30 $\mu$g/ml for Rhodococcus) and to thiostrepton (50 $\mu$g/ml for Rhodococcus). Plasmid content was verified by small-scale plasmid preparations.

DNA Biochemistry

Restriction endonuclease digestions were performed as per the manufacturer's directions. Restriction enzymes were purchased from Boehringer Mannheim Biochemicals, New England Bio Labs or Bethesda Research Laboratories. Plasmid restriction mapping was performed using a series of single and multiple restriction digestions of plasmid DNA. DNA fragments were separated by horizontal gel electrophoresis using gels prepared with 0.7% (wt/vol) agarose (International Biotechnologies, Inc.) or with 4.0%) (wt/vol) Nu-Seive agarose (FMC Bioproducts) to resolve small DNA fragments, using 0.04M Tris-acetate, 0.002M EDTA electrophoresis buffer, pH 8.0 at 100 volts or 50 volts, respectively. Gels were stained with ethidium bromide (0.5 µg/ml) and DNA was visualized with ultraviolet light. DNA fragment size was determined by comparison with HindIII-digested linear phage Lambda DNA fragments and with a 1 kilobase ladder linear DNA standard (Bethesda Research Laboratories).

Ligations were performed with T4 DNA ligase (Boehringer Mannheim Biochemicals) and alkaline phosphatase (Boehringer Mannheim Biochemicals), as per the manufacturer's instructions.

Colony Hybridization

E. coli transformants were transferred to nitrocellulose filters and were lysed on the filter by the method of Grunstein and Hogness, Proc. Natl. Acad. Sci. 72, 3961–3965 (1975). Filters were prehybridized at 37° C. for 2 h in a buffer containing 6×SSC (1×SSC is 0.15M NaCl 0.015M sodium citrate) plus 50% (vol/vol) formamide, 0.1% (wt/vol) SDS and 50 µg/ml denatured salmon sperm DNA. The $^{32}$P-labeled probe was prepared by nick translation of plasmid DNA with [α-$^{32}$P]dATP, Maniatis et al, Molecular Cloning. A Laboratory Manual. (Cold Spring Harbor Laboratory, New York 1982). The $^{32}$P-labeled probe was purified by Sephadex G-25 chromatography, denatured and hybridized to DNA immobilized on the filters in fresh prehybridization buffer at 37° C. for 18 h. After hybridization, the filters were washed at 37° C. in succession with 6×SSC, 2×SSC, 1×SSC and 0.2×SSC, each buffer containing 50% (vol/vol) formamide. Autoradiography was performed using Kodak XAR-5 film developed at −80° C. for 18 h with an intensifying screen.

Southern Hybridization

Transfer of DNA from agarose gels to nitrocellulose and Southern hybridization with the $^{32}$P-labeled probe, prepared by nick translation of a purified plasmid restriction fragment, was performed as per Maniatis, et al.

Measurement of β-lactamase activity

β-lactamase activity was measured with the chromogenic β-lactamase substrate, PADAC, (7-(thienyl-2-acetamide)-3[-2(4-N,N-dimethylaminophenylazo)-pyridinium methyl]-3-cephem-4-carboxylic acid), described by Shindler and Huber, Proc. Enzyme Inhibitors, Basel Verlag Chemie, Weinheim, U. Brodbeck, ed., p. 169–176 (1980). NBYE-or LB-grown cells were suspended in 20 mM Tris-chloride buffer, pH 8.0. The reaction was started by addition of 0.1 ml cells or culture supernatant to 0.9 ml 25 µM PADAC in 20 mM Tris-chloride buffer, pH 8.0. β-lactamase activity was measured by monitoring the decrease in optical density at 570 nm at 30° C. Intact cells were treated prior to measurement of enzyme activity by addition of 10% toluene and 0.1% sodium deoxycholate.

Cell protein was measured by the method of Lowry, et al., J. Biol. Chem. 193, 265–275 (1951) using bovine serum albumin as standard.

Modifications and variations of the present invention, a cloning system for Rhodococcus and related bacteria, will be apparent to those skilled in the art from the foregoing detailed description in combination with Rhodococcus ATCC 53719 deposited Feb. 1, 1988. Such variations and modifications are intended to come within the scope of the appended claims.

We claim:

1. A cloning vector comprising:
   an origin of replication as present in plasmid pMVS301 in Rhodococcus AS50-1 (pMVS100, pMVS200, pMVS301) ATCC 53719 deposited Feb. 1, 1988.

2. The cloning vector of claim 1 wherein the origin of replication is in a plasmid.

3. The cloning vector of claim 2 wherein the plasmid is selected from the group consisting of pMVS301, (ATCC 53719) pMVS302, pMVS301KC, and pMVS301KA.

4. The cloning vector of claim 2 wherein the plasmid contains nucleic acid sequences in addition to the sequences contained in pMVS301 (ATCC 53719).

5. The cloning vector of claim 2 further comprising a nucleic acid sequence encoding a protein.

6. The cloning vector of claim 3 further comprising an origin of replication for a bacteria in a genus other than Rhodococcus.

7. The cloning vector of claim 6 wherein the non-Rhodococcus origin of replication is an E. coli origin of replication.

8. A host selected from the group consisting of Rhodococcus sp., Actinomyces, Nocardia, Mycobateria, and Streptomyces haboring the vector of claim 1.

9. The cloning vector of claim 8 wherein the host is Rhodococcus AS50-1 (pMVS100, pMVS200, pMVS301) (ATCC 53719).

10. A method for cloning and expressing nucleic acid sequences in Rhodococcus and related bacteria capable of using the same origin of replication comprising:
    providing a vector capable of stable replication in Rhodococcus containing an origin of replication for use in Rhodococcus present in Rhodococcus AS50-1 (pMVS100, pMVS200, pMVS301) (ATCC 53719);
    transforming a host bacteria capable of recognizing the Rhodococcus origin of replication; and
    culturing the transformed host bacteria under conditions wherein nucleic acid sequences are expressed.

11. The method of claim 10 wherein the vector is a plasmid.

12. The method of claim 11 wherein the plasmid is selected from the group consisting of pMVS301, (ATCC 53719) pMVS302, pMVS301KC, pMVS301KA and derivatives of these plasmids containing the pMVS301 origin of replication.

13. The method of claim 11 further comprising:
    providing a sequence encoding a gene and inserting the sequence into the plasmid.

14. The method of claim 10 further comprising providing a host selected from the group consisting of Rhodococcus sp., Actinomyces, Nocardia, Mycobacteria, and Streptomyces.

15. The method of claim 14 wherein the host is selected from the group consisting of Rhodococcus AS50-1 (pMVS301) ATCC 53719 deposited Feb. 1, 1988 and derivatives thereof, R. equi, R. erythropolis, and R. globulerus.

16. The method of claim 11 further comprising providing a gene for antibiotic resistance in the plasmid.

17. The method of claim 10 wherein the origin of replication is selected from the origins of replication in plasmids pMVS100 and pMVS200.

* * * * *

UNITED STATES PATENT AND TRADEMARK OFFICE
CERTIFICATE OF CORRECTION

PATENT NO. : 4,952,500
DATED : Aug. 28, 1990
INVENTOR(S) : William R. Finnerty, Mary E. Singer It is certified that error appears in the above-identified patent and that said Letters Patent is hereby corrected as shown below:

Col. 2, line 66: Replace "Rhdococcus" with —Rhodococcus—.
Col. 6, line 64: Replace "in" with —and—.
Col. 7, line 50: Replace "MVS200)" with —pMVS200)—.
Col. 7, line 56: Replace "(MVS100" with —(pMVS100—.
Col. 8, line 28: Replace "(MVS302)" with —(pMVS302)—.
Col. 8, line 31: Replace "(MVS302)" with —(pMVS302)—.
Col. 8, line 50: Replace "clacarea" with —calcarea—.
Col. 14, line 27: Replace "Mycobateria" with —Mycobacteria—.
Col. 14, line 28: Replace "haboring" with —harboring—.

Signed and Sealed this

Eighth Day of November, 1994

*Attest:*

BRUCE LEHMAN

*Attesting Officer*     Commissioner of Patents and Trademarks